United States Patent [19]
Yoshimatsu et al.

[11] Patent Number: 5,212,506
[45] Date of Patent: May 18, 1993

[54] ANALYSIS METHOD OF EYEBALL CONTROL SYSTEM

[75] Inventors: Hiroshi Yoshimatsu; Mitsuho Yamada, both of Kyoto, Japan

[73] Assignee: ATR Auditory and Visual Perception Research Laboratories, Kyogo, Japan

[21] Appl. No.: 760,442

[22] Filed: Sep. 17, 1991

[30] Foreign Application Priority Data

Nov. 27, 1990 [JP] Japan ................................ 2-326283

[51] Int. Cl.$^5$ .............................................. A61B 3/10
[52] U.S. Cl. .................................... 351/210; 351/246
[58] Field of Search ......................... 351/209, 210, 246

[56] References Cited

U.S. PATENT DOCUMENTS 4,973,149  11/1990  Hutchinson ......................... 351/210
5,002,384  3/1991   Trachtman .......................... 351/210

OTHER PUBLICATIONS

Mitsuho Yamada et al., "Defining of Gazing Point for Picture Analysis and Its Applications", *Systems and Computers in Japan*, vol. 18, No. 8, 1987, pp. 88–96 (no month avail.).

Thomas C. Halsey et al., "Fractal Measures and their Singularities: The Characterization of Strange Sets", *Physical Review A* (The American Physical Society), vol. 33, No. 2, Feb. 1986, pp. 1141–1151.

David M. Drouin et al., "A Fiber Optic Eye Position Sensor", Proceedings of the 13th Annual Northeast Bioengineering Conference, vol. 1, Mar. 12, 1987, pp. 181–184.

*Primary Examiner*—Rodney B. Bovernick
*Attorney, Agent, or Firm*—Lowe, Price, LeBlanc & Becker

[57] ABSTRACT

Flicks in one or both of eyes are measured by a sensor (1) employing a limbus reflection method. An output of the sensor is applied to and digitized by an A/D converter (2). The digitized output is applied to a computer (3). The computer calculates flicks data of eyeballs, then calculates fractal dimension simultaneously or individually in a time-elapsed manner or for a definite time period, and quantifies characteristics of the eyeball control systems from the value of the fractal dimension or the time dependence of the fractal dimension.

7 Claims, 7 Drawing Sheets

ANALYSIS METHOD OF EYEBALL CONTROL SYSTEM

BACKGROUND OF THE INVENTION

1. Field of the Invention

The present invention relates generally to analysis methods of an eyeball control system and, more particularly, to an analysis method of eyeball control system that can be employed for a more quantitative diagnosis method in ophthalmology and psychoneurology in medical engineering and for quantitative evaluation of visual psychological experiments in psychology.

2. Description of the Background Art

Even if one's eyes are fixed on one point, a visual axis of the eyes makes small constant movement. This small movement is known as small involuntary eye movement, called flicks. The flicks are classified in detail as follows: ①. A small oscillation with an amplitude angle of approximately 15" and a frequency band of 30–100 Hz in small movement; ②. Flicks generated in the form of step or pulse at the angle of anomaly of approximately 20' in an irregular period of 0.03-5 sec.; and ③. Drifts known as a slow kinetic component which is produced during the flicks at the angle of anomaly of approximately 5' or less. Conventionally, since flicks have a small amplitude and high speed, it has been difficult to precisely measure the flicks in modeling a control system thereof by employing transmission function or the like, and hence the flicks have been regarded simply as random oscillation. Thus, although numerous models have been proposed with respect to control characteristics of ocular movement except for the flicks, there have been few similar models for the flicks.

SUMMARY OF THE INVENTION

A principal object of the present invention is therefore to provide an analysis method of an eyeball control system that makes it possible to numerically represent the characteristics of an eyeball control system by using fractal dimension and implement quantitative evaluation as evaluation parameters of the eyeball control system.

Briefly, according to the present invention, small oscillation is measured by focusing on a small amplitude included in the eyeball control system of eyes, fractal dimension is calculated in accordance with the measured small oscillation, and the characteristics of the eyeball control system are quantified in accordance with the calculated fractal dimension.

Therefore, according to the present invention, eyeball information included in the small movement that has been almost ignored and regarded as noise can be efficiently quantified from a fractal dimension analysis or multi-fractal. This makes it possible to examine a clinical diagnosis, curative effects and the like in ocular or mental diseases by an extremely short-time calculation. In a field of psychology, the use of measurement of an eyeball control system upon a visual psychological experiment makes it possible to quantitatively evaluate results of the experiment by using fractal dimension.

According to a more preferable embodiment of the present invention, small oscillation is output as time-serial two-dimensional data, the dimension of phase space is then set on the basis of the two-dimensional data, and correlation dimension is calculated on the basis of the set dimension of the phase space.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
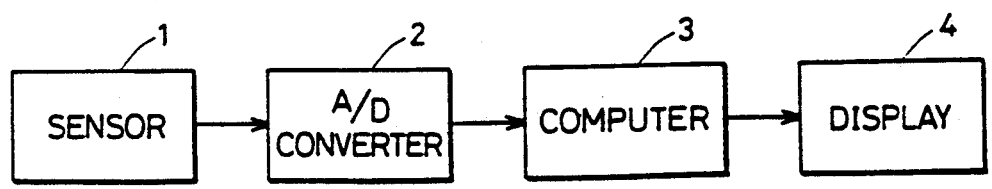
FIG. 1 is a schematic block diagram of one embodiment of the present invention.
Figure 2:
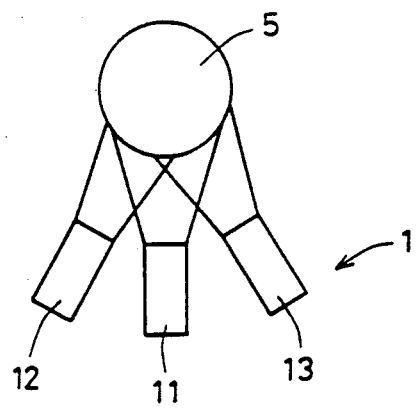
FIGS. 2 and 3(a)–(b) are diagrams for use in explaining a method of measuring flicks of an eyeball by using a limbus reflection method.
Figure 3A:
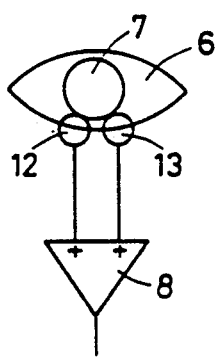
Figure 3B:
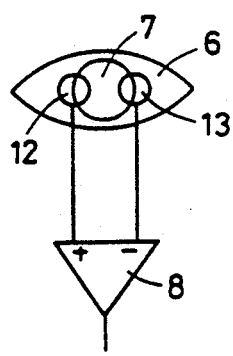

A construction of one embodiment of the present invention will now be described with reference to FIGS. 1-3. A sensor 1 serves to measure flicks of an eyeball by using a limbus reflection method. As shown in FIG. 2, when a subject is looking at a target not shown, sensor 1 illuminates an eyeball 5 of the subject with infrared light emitted from a light emitting diode 11, and then detects the amount of reflected light at the boundary between a white part 6 and a colored part 7 of the eye by left and right photodiodes 12 and 13 as shown in FIG. 3. More specifically, vertical flicks of the eye can be detected from a sensor amplifier 8 by detecting the amount of reflected light at the boundary between white part 6 and a lower portion of colored part 7 by using photodiodes 12 and 13 as shown in FIG. 3(a). Furthermore, horizontal flicks of the eye can be detected from sensor amplifier 8 by detecting the amount of reflected light at the boundary between white part 6 and horizontal opposite ends of colored part 7 by using photodiodes 12 and 13 as shown in FIG. 3(b).

An output of sensor amplifier 8 is applied to an A/D converter 2. The applied output is digitized by A/D converter 2 and then applied to a computer 3. Computer 3 processes flicks data of eyeball 5 by calculation, then obtains a fractal dimension value and time dependence of the fractal dimension and displays the results on a display device 4.

Figure 4:
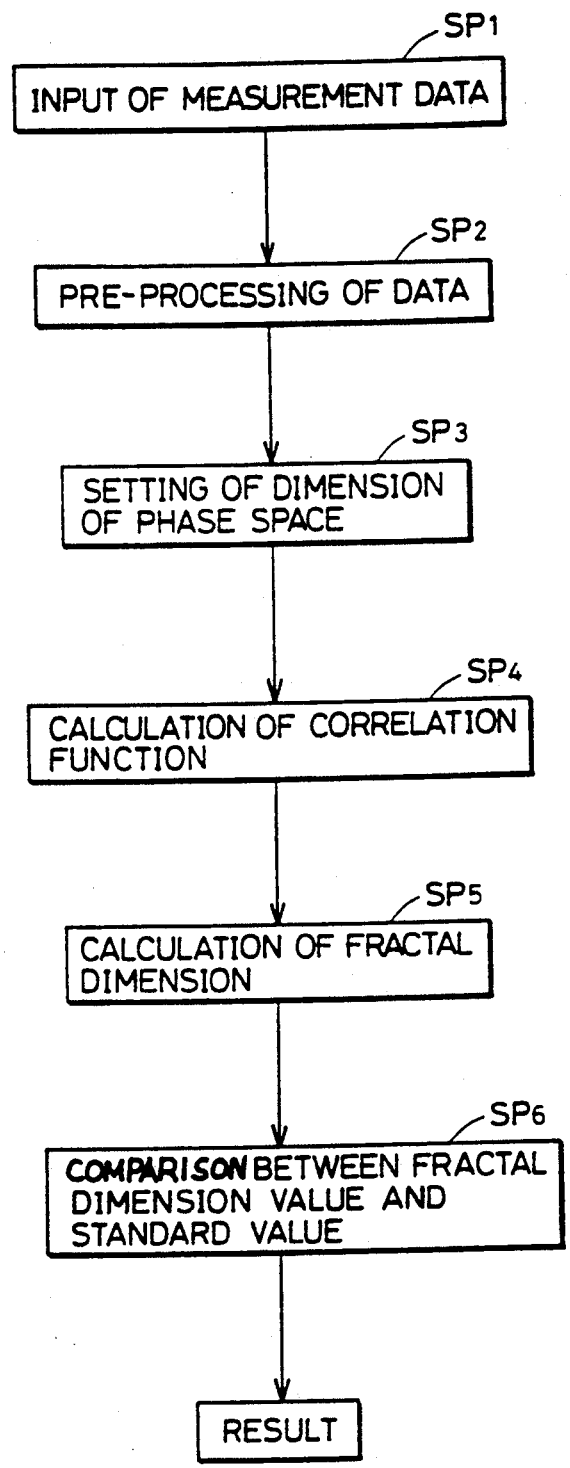
FIG. 4 is a flow chart for use in explaining an operation of the above embodiment of the present invention.

FIG. 4 is a flow chart for use in explaining an operation of the embodiment of the present invention. A detailed operation of the embodiment will now be described with reference to FIGS. 1-4. Computer 3 accepts the flicks data digitized by A/D converter 2 as time-serial two-dimensional sampling data at step SP1 and carries out pre-processing of the data at step SP2. The flicks data includes a very slow small movement of a head, a saccade that is not produced frequently but occurs with a great deviation from the target, a nictitation component and the like. If the flicks data includes other components than flicks in presuming degrees of freedom in the flicks, those components are over-evaluated as the degrees of freedom of a system. Accordingly, great waviness close to a direct current component, a component corresponding to saccade that is produced sometimes and has an extremely large amplitude, and the like are removed.

The above-described two-dimensional data corresponds to coordinates of an arbitrary coordinate system, i.e., a polar coordinate system or orthogonal coordinate system. The fractal dimension of flicks is derived with one of these coordinate values being x (t). In the fractal dimension, geometric representation of distribution of data such as a locus of a corresponding system is quantified. For example, if data is distributed in a linear manner, its fractal dimension becomes almost one dimension. If the data is arranged in a planar manner, the fractal dimension becomes two dimensions. Further, if the data is overlapped with each other on a curved surface, then the fractal dimension becomes at least two and less than three dimensions. If the data is distributed completely spatially, then the fractal dimension becomes three dimensions.

It is known that fractal dimension is approximately equal to the degree of freedom of its system. In the case with complete noise, the fractal dimension becomes infinite. More specifically, even if data seems random at sight, when the fractal dimension of the data is not infinite but finite, it is highly possible that the data is not noise. Calculating the fractal dimension makes it possible to presume a minimum degree of internal freedom required to describe the system.

As a method of calculating fractal dimension with simplification by employing non-serial sampling data, there is a method described, for example, in *Phys. Lett.*, Vol. 114A (5), pages 217–221 (1986) by N. B. Abraham et al. In order to obtain correlation dimension, computer 3 produces phase space from pre-processed data. In a method for producing phase space from time-serial data, time-serial one-dimensional data is x (t), an appropriate sampling period $\Delta t = (t_{i+1} - t_i)$ is selected from the one dimensional data, and a discrete data point sequence $\{x_{i=x(ti)}:i=1 \ldots N\}$ is generated.

Then, computer 3 sets the dimension of the phase space at step SP3. That is, according to the equation $X_1=(i)=(x_i, x_{i+1})$ wherein $i=1, 3, \ldots, 2n+1, \ldots, N-1$, $X_1$ paired with $x_i$ is obtained. An orbit X on pseudo-phase space is topologically identical to (x (t), v (t)) on phase space wherein v (t) is time differential (speed) of x (t).

Then, computer 3 performs a calculation of correlation function at step SP4. More specifically, computer 3 calculates a correlation dimension defined in the following as fractal dimension with respect to a data point set on pseudo-phase space in accordance with the above-described method by N. B. Abraham et al.

Definitions of correlation dimension:

frac. dim = log (C(r))/log(r)

wherein C (r) is correlation function, and r is a distance between the respective data points.

$$C(r) = \lim_{N \to \infty} 1/N^2 \cdot \sum_{i}^{N} \sum_{j}^{N} H(r - |x_i - x_j|) \quad (1)$$

wherein $x_i$ is the position of a measured point at time $t_i$, and H (r) is Heaviside step function where the following relation is satisfied:

$$H(x) = \begin{cases} 0 & x < 0 \\ 1 & x > 0 \end{cases} \quad (2)$$

If flicks are measured as described above, computer 3 calculates fractal dimension at step SP5, then compares the value of the fractal dimension with a pre-measured standard value of a healthy person or the value of a patient at step SP6, and displays the result on display device 4.

Figure 5:
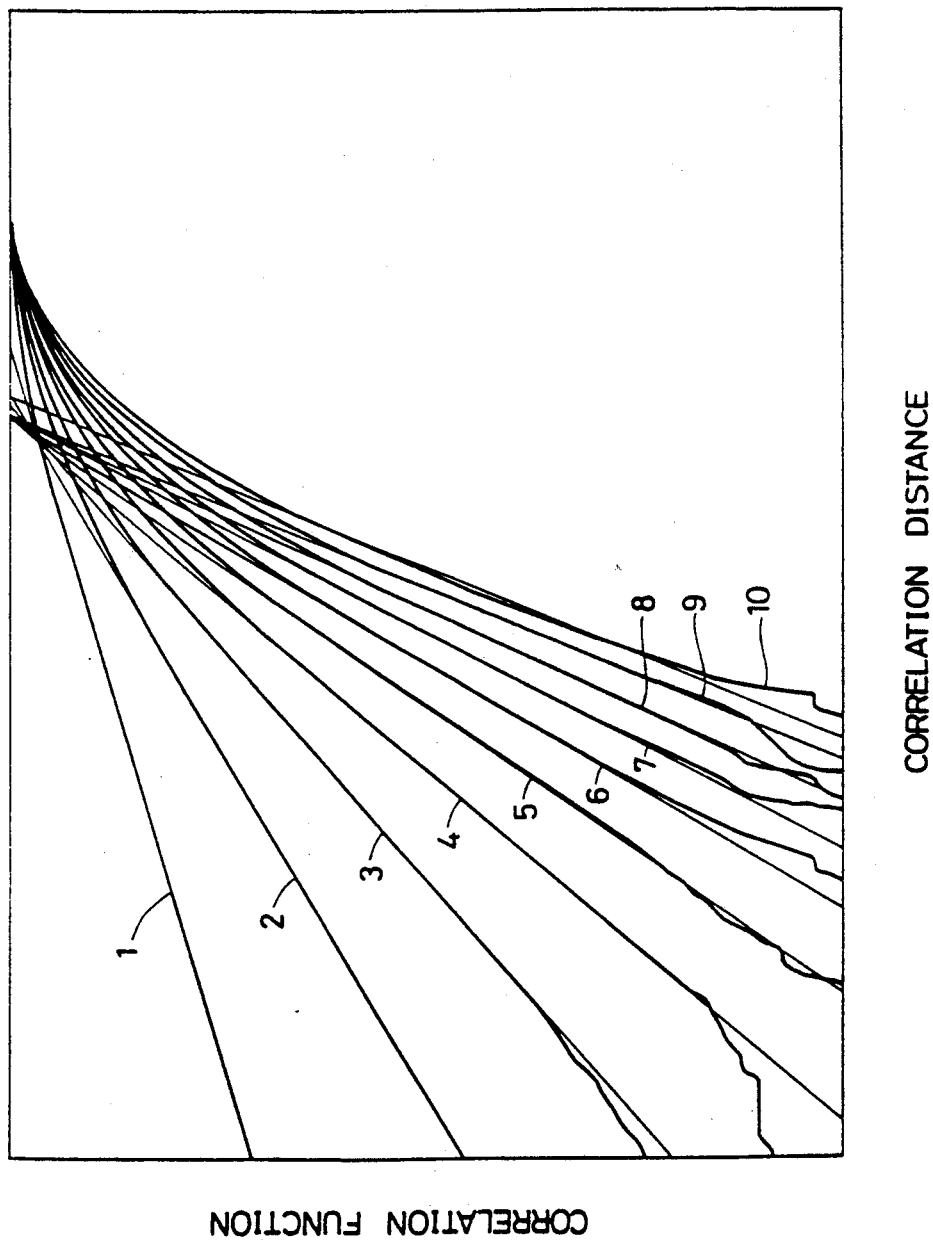
FIG. 5 is a diagram showing the relationship between correlation distance and correlation function obtained in the above embodiment of the present invention.

FIG. 5 is a diagram showing the relationship between correlation distance and correlation function obtained in the embodiment shown in FIG. 4. In FIG. 5, the abscissa indicates correlation distances and the ordinate indicates correlation functions, showing the respective characteristics of one to ten fractal dimensions. The inclination of the characteristics of each dimension is the value of the fractal dimension.

Figure 6:
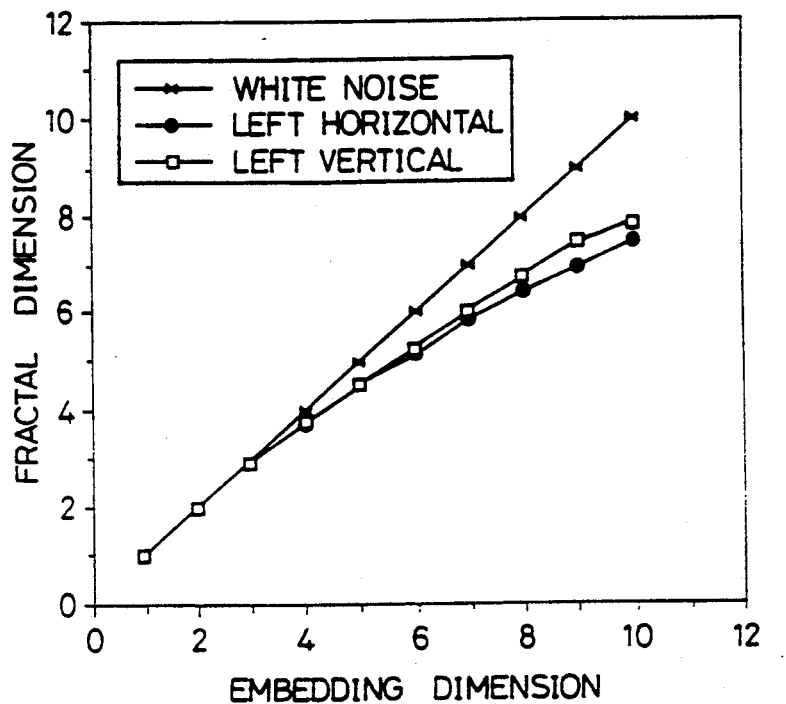
FIG. 6 is a diagram showing dependence of fractal dimension on embedding dimension with respect to horizontal and vertical directions of a left eye.
Figure 7:
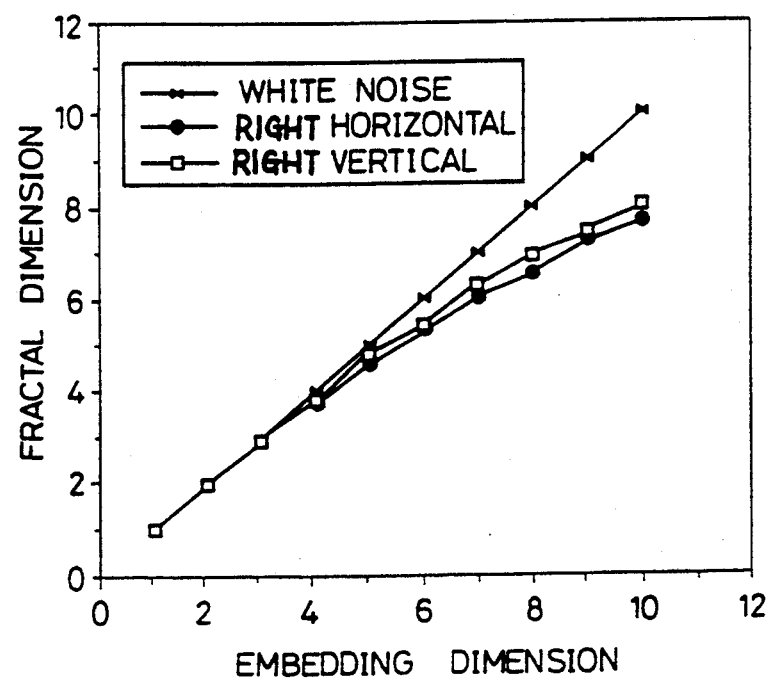
FIG. 7 is a diagram showing dependence of fractal dimension on embedding dimension with respect to horizontal and vertical directions of a right eye.

FIG. 6 is a diagram showing dependence of fractal dimension on embedding dimension, in which the fractal dimension is calculated with one to ten embedding dimensions with respect to the horizontal and vertical directions of a left eye. FIG. 7 is a diagram showing dependence of the fractal dimension on the embedding dimension, in which the fractal dimension is calculated with one to ten embedding dimensions with respect to the horizontal and vertical directions of a right eye.

In FIGS. 6 and 7, the abscissa indicates one to ten embedding dimensions, and the ordinate indicates the fractal dimension. FIG. 6 shows the correlation between white noise and the left horizontal and vertical directions.

FIG. 7 shows the correlation between the right horizontal and vertical directions.

As apparent from FIGS. 6 and 7, while both the left and right fractal dimensions are apparently different from the white noise, the fractal dimensions represent a positive correlation close to the white noise. This suggests that a noise-like component is included in a drift component of flicks. With regard to both the left and right eyes, a higher fractal dimension is indicated in the vertical direction rather than the horizontal direction. It is presumed that this is because of differences in ratio of the noise-like component or because the fractal dimension of the system is actually higher in the vertical direction.

Figure 8:
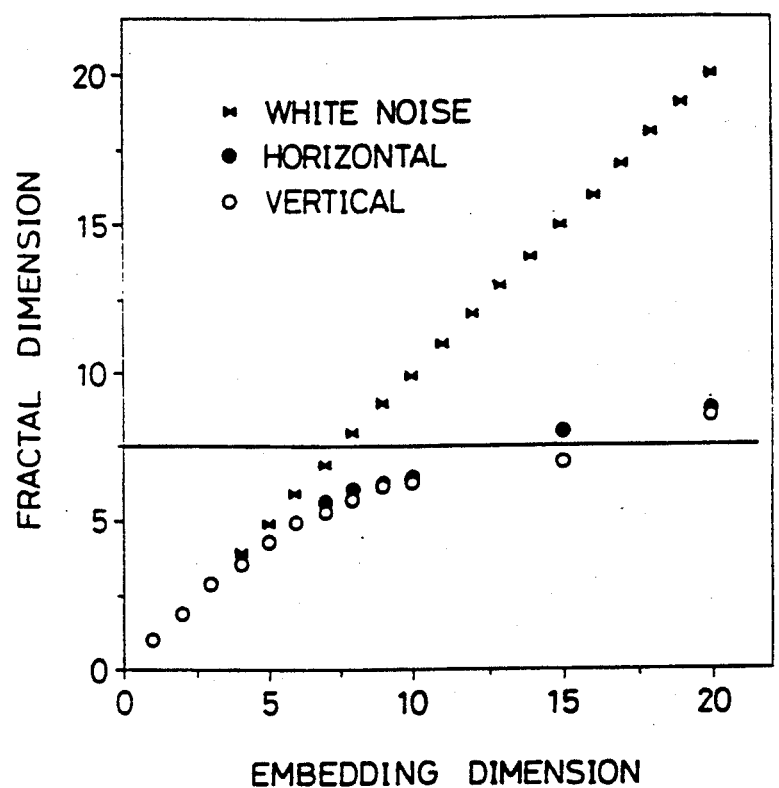
FIG. 8 is a diagram showing fractal dimension of a drift component of the difference between left and right eyes in horizontal and vertical directions.

FIG. 8 is a diagram showing the fractal dimension of a drift component of the difference between left and right eyes in the horizontal and vertical directions. In an example shown in FIG. 8, left-eye data and right-eye data are input as measurement data of FIG. 4, and the difference between the left and right data is obtained to calculate fractal dimension. As apparent from FIG. 8, the fractal dimension of drifts in the horizontal direction is always approximately 0.5 dimensions higher than the fractal dimension of drifts in the vertical direction. With regard to both the horizontal and vertical directions, embedding dimension starts to be saturated around dimensions higher than five. When embedding dimensions are 15 or 20, the fractal dimension is converged on approximately 7.5 dimensions.

The fractal dimension may be calculated by oscillating the target looked by the subject and measuring how eyeball movement, saccade in particular follows the movement of the target. If the eyeball movement completely follows the movement of the target, the fractal dimension is one.

Further, according to "Fluctuations in Accommodation: A Review", *Ophthal. Physiol. Opt.*, 1988, 8, pages 153–164 by W. N. Charman, there is a small oscillation movement (small movement in accommodation) corresponding to flicks in eyeball movement with respect to accommodation also, and such movement is regarded as noise. Thus, fractal dimension of small oscillation may be analyzed by employing the present invention.

In addition, according to *IEEE., BME*-13, 1966, pages 140–152 by S. F. Stanten & L. Stark, a noise component that always exists at a frequency of approximately 2 Hz of a normal pupil movement is confirmed, and fractal dimension of such a noise component may be calculated. A pupil system in particular is controlled by an autonomic nervous system and is available for evaluations (quantifications) in diagnoses of mental diseases or curative effects of various internal medicine diseases as well as in a field of ophthalmology.

Figure 9:
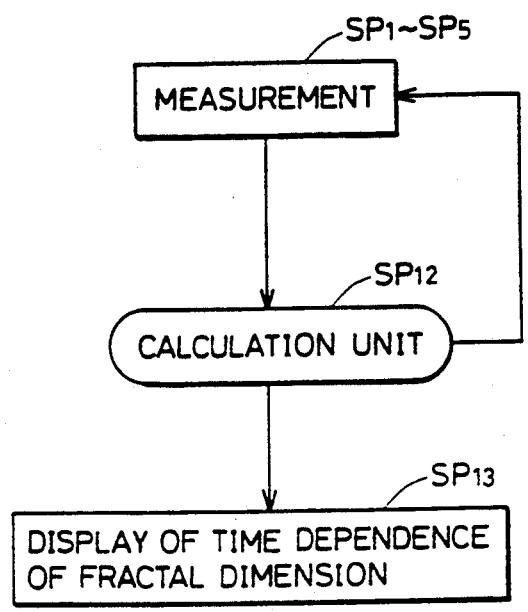
FIG. 9 is a flow chart for use in explaining another embodiment of the present invention.

FIG. 9 is a flow chart showing another embodiment of the present invention. In the embodiment shown in FIG. 9, steps SP1–SP5 shown in FIG. 4, which is from the input of measurement data to the calculation of fractal dimension, is used, time dependence of the fractal dimension is analyzed with respect to both the left and right eyeball control systems at the same time at step SP12, and an overall index of eyeballs is obtained as a system from its correlation relationship at step SP13. That is, data is sampled at appropriate intervals, and fractal dimension is calculated on the basis of the data provided at the intervals.

Figure 10:
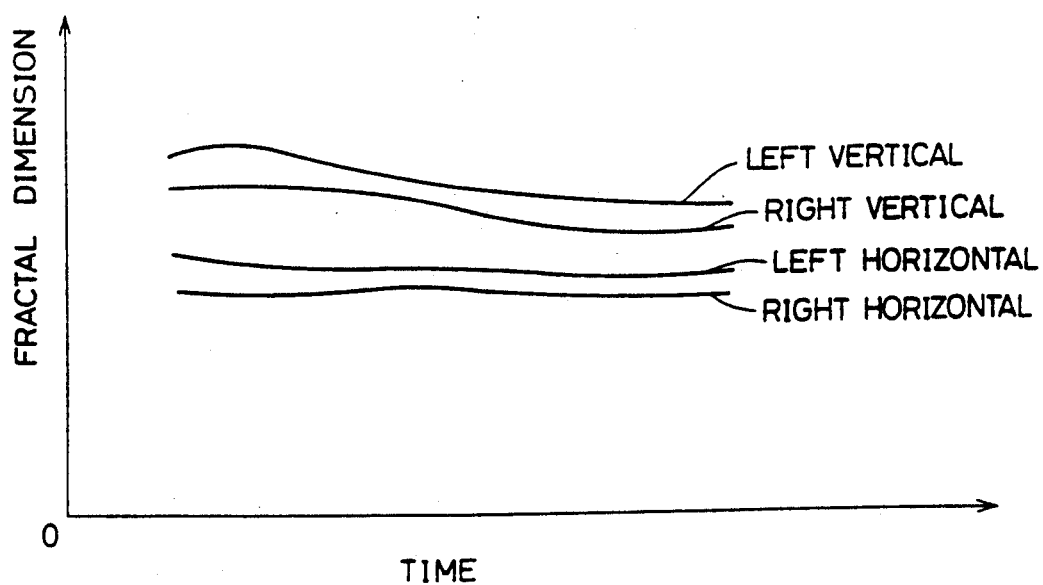
FIG. 10 is a diagram showing fractal dimension depending on time obtained in the embodiment shown in FIG. 9.

FIG. 10 is a plot of the vertical and horizontal fractal dimensions of the left and right eyeballs obtained in the embodiment shown in FIG. 9. The abscissa indicates times and the ordinate indicates fractal dimensions in FIG. 10, in which data is sampled at appropriate intervals, left and right fractal dimensions at respective times are calculated and plotted, and interpolation is made between the respective fractal dimensions. As apparent from FIG. 10, the fractal dimensions become lower with an elapse of times. This suggests that with the elapse of time, the eyes are fatigued and flicks become decreased.

Figure 11:
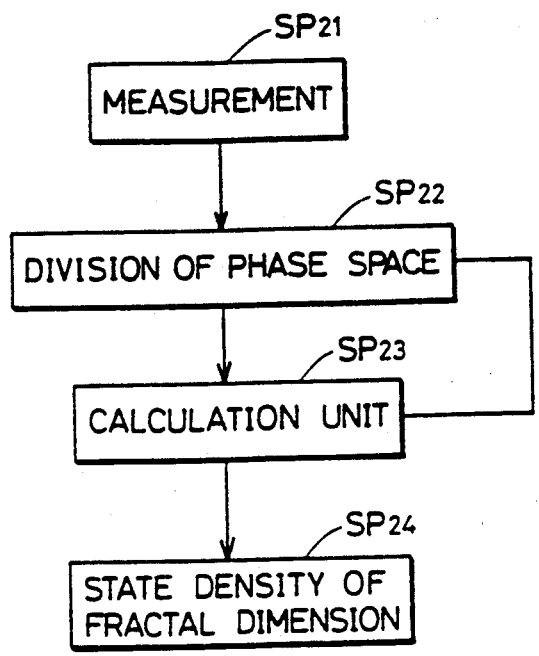
FIG. 11 is a diagram showing still another embodiment of the present invention.
Figure 12:
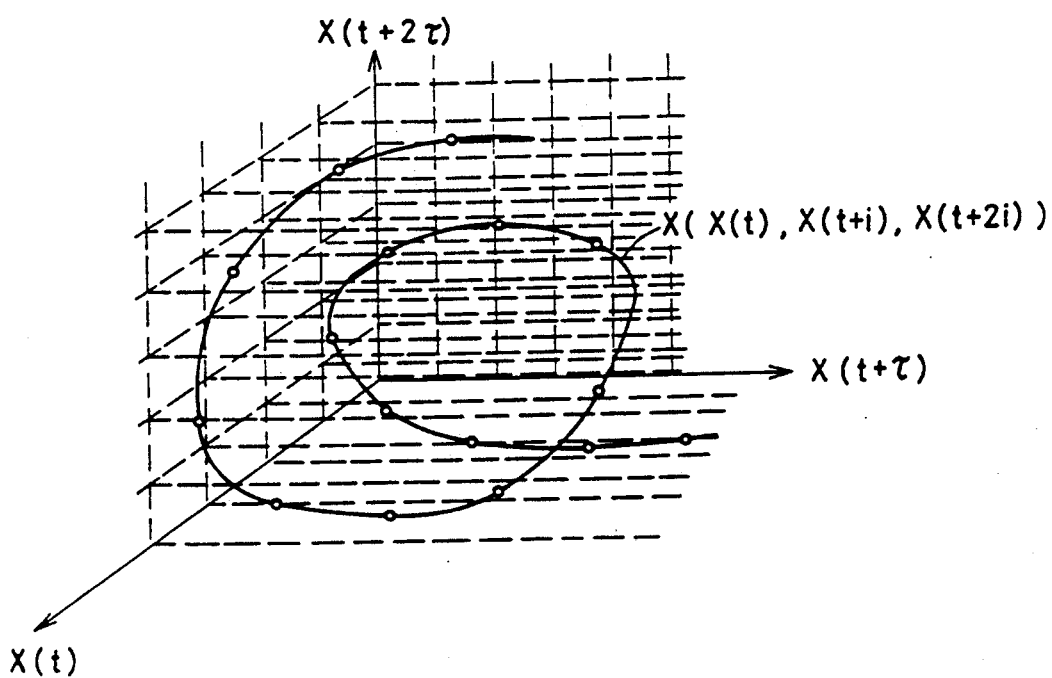
FIG. 12 is a diagram showing distribution of fractal dimension of phase space obtained in the embodiment shown in FIG. 11.

FIG. 11 is a flow chart showing still another embodiment of the present invention. FIG. 12 is a diagram showing distribution of fractal dimension in phase space obtained in the embodiment shown in FIG. 11.

In the embodiment of FIG. 11, distribution of fractal dimension in phase space is investigated by using an f ($\alpha$) spectrum (T. C. Halsey et al.: *Phys. Rev.*, A33 (1986), 1141) that features a multi-fractal structure as an expanded concept of fractal dimension.

In each of the foregoing embodiments, since the fractal dimensions are calculated with respect to the entire set of data points in phase space, a fluctuation of fractal dimension in each portion in phase space is neglected. In the multi-fractal structure, since distribution density of fractal dimension in phase space is taken into account, precise numerical representation is enabled. More specifically, as shown in FIG. 12, the phase space is represented by coordinates of $x(t)$, $x(t+\tau)$ and $x(t+2\tau)$ wherein $\tau$ is periods. Fractal dimensions represented by $x(t)$, $x(t+\tau)$ and $x(t+2\tau)$ are illustrated in this phase space. Thus, measurement of data in the phase space is made at one time, and the space is divided into subspaces as shown by dotted lines of FIG. 12 at step SP22, whereby fractal dimensions are calculated in the respective subspaces at step SP23.

As has been described heretofore, according to the embodiments of the present invention, a small amplitude of each of various eyeball control systems is measured, whereby information of eyeballs included in small eyeball movement that has conventionally been neglected and regarded as noise can be quantified with high efficiency from a fractal dimension analysis or multi-fractal. Consequently, a clinical diagnosis, curative effects and the like in ocular and mental diseases can be examined by a very short-time calculation. In addition, in the field of psychology, the use of measurement of eyeball control systems upon visual psychological experiments makes it possible to quantitively evaluate the results of the experiments by using fractal dimension.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A method for analyzing small oscillations of an eye to enable quantifying said small oscillations, comprising the steps of:
   measuring small eye oscillations while an eye of a subject is looking at a target and providing output signals corresponding thereto, said small eye oscillations having small amplitudes;
   converting said output signals to digital signals;
   inputting said digital signals to a computer;
   calculating fractal dimension for said measured small eye oscillations using said digital signals;
   providing a quantity using said fractal dimension which corresponds to said small oscillations of the eye; and
   displaying the quantity on a display means,
   using said quantity to accurately model an eyeball control system.

2. The method according to claim 1, wherein providing output signals includes outputting said output signals as time-serial two-dimensional data.

3. The method according to claim 2, wherein said step of calculating fractal dimension includes setting dimension of phase space in accordance with said time-serial two-dimensional data.

4. The method according to claim 3, wherein said step of calculating fractal dimension further includes calculating correlation dimension in accordance with said set dimension of phase space.

5. The method according to claim 3, wherein said step of providing a quantity includes comparing said calculated fractal dimension with a predetermined standard value.

6. The method according to claim 1, wherein said eyeball control system includes a left eyeball control system and a right eyeball control system, said step of measuring small eye oscillations includes separately measuring small eye oscillations of left and right eyes, and said step of providing a quantity includes analyzing time dependence of the calculated fractal dimension with respect to said eyeball control system and said right eyeball control system at a time corresponding to the measured small eye oscillations of said left and right eyes, respectively.

7. The method according to claim 3, wherein said step of calculating fractal dimension further includes dividing the phase space into subspaces and calculating fractal dimension in each subspace.

* * * * *